United States Patent
Whitaker

(10) Patent No.: US 10,859,192 B2
(45) Date of Patent: Dec. 8, 2020

(54) REUSABLE CLAMP WITH LATCH RELEASE ARM FOR CONNECTING CONDUIT SECTIONS AND ASSOCIATED METHODS

(71) Applicant: NORDSON CORPORATION, Westlake, OH (US)

(72) Inventor: Carl T. Whitaker, Berthoud, CO (US)

(73) Assignee: Nordson Corporation, Westlake, OH (US)

( * ) Notice: Subject to any disclaimer, the term of this patent is extended or adjusted under 35 U.S.C. 154(b) by 19 days.

(21) Appl. No.: 16/178,751

(22) Filed: Nov. 2, 2018

(65) Prior Publication Data
US 2019/0072217 A1 Mar. 7, 2019

Related U.S. Application Data

(62) Division of application No. 14/810,960, filed on Jul. 28, 2015, now Pat. No. 10,125,906.
(Continued)

(51) Int. Cl.
*A61M 39/28* (2006.01)
*F16L 25/00* (2006.01)
(Continued)

(52) U.S. Cl.
CPC ........... *F16L 25/009* (2013.01); *A61M 39/28* (2013.01); *A61M 39/284* (2013.01); *F16L 23/04* (2013.01);
(Continued)

(58) Field of Classification Search
CPC ......... F16L 23/04; F16L 21/06; F16L 21/065; A61M 39/10; B29C 65/56; Y10T 29/53987
(Continued)

(56) References Cited

U.S. PATENT DOCUMENTS

| 1,441,154 A | 1/1923 | Johnson |
| 3,913,187 A | 10/1975 | Okuda |

(Continued)

FOREIGN PATENT DOCUMENTS

| CN | 1516786 A | 7/2004 |
| CN | 201891942 U | 7/2011 |

(Continued)

OTHER PUBLICATIONS

English Translation of JP Office Action dated Jul. 9, 2019 for JP Application No. 2015161642.
(Continued)

*Primary Examiner* — Lawrence Averick
(74) *Attorney, Agent, or Firm* — Baker & Hostetler LLP

(57) ABSTRACT

A reusable clamp for retaining conduit sections or sanitary fittings having circular flanges together includes two gland members movable between open and closed positions. The gland members include two handles projecting outwardly from the gland members and two sets of locking detents formed on a latch finger connected to one gland member and the outer periphery of the other gland member. The locking detents engage to prevent movement of the gland members away from the closed position until a latch release arm coupled to the latch finger is depressed towards one of the handles, which causes the locking detents to disengage from one another and enables re-opening of the clamp when desired. The latch release arm and one or more of the handles also include tie-receiving loops to prevent accidental opening of the clamp unless desired by the end user.

14 Claims, 10 Drawing Sheets

Related U.S. Application Data

(60) Provisional application No. 62/040,150, filed on Aug. 21, 2014.

(51) Int. Cl.
  *F16L 37/12* (2006.01)
  *F16L 23/04* (2006.01)
  *F16L 25/06* (2006.01)

(52) U.S. Cl.
  CPC ............... *F16L 25/06* (2013.01); *F16L 37/12* (2013.01); *F16L 37/1225* (2013.01); *F16L 2201/44* (2013.01)

(58) Field of Classification Search
  USPC ............. 285/407, 419, 420; 24/16 PB, 17 A, 24/17 AP; 29/525.08, 525.01
  See application file for complete search history.

(56) References Cited

U.S. PATENT DOCUMENTS

| | | |
|---|---|---|
| 4,511,164 A | 4/1985 | Orchard |
| 5,305,978 A | 4/1994 | Current |
| 6,488,664 B1* | 12/2002 | Solomon ........... A61M 16/0666 24/20 R |
| 6,742,223 B1 | 6/2004 | Chang |
| 6,898,825 B1 | 5/2005 | Charest |
| 6,978,973 B1 | 12/2005 | Gretz |
| 8,328,457 B2 | 12/2012 | Werth |
| 8,328,458 B2 | 12/2012 | Werth |
| D695,100 S | 12/2013 | Whitaker et al. |
| 8,827,214 B2 | 9/2014 | Ogawa |
| 9,004,545 B2 | 4/2015 | Whitaker et al. |
| D749,835 S | 2/2016 | Whitaker |
| D770,886 S | 11/2016 | Whitaker |
| 2004/0159454 A1* | 8/2004 | Shibuya ............ B60R 16/0215 174/545 |
| 2009/0119886 A1 | 5/2009 | Werth |
| 2009/0208277 A1 | 8/2009 | Werth |
| 2010/0060460 A1 | 3/2010 | Zinner |
| 2010/0268161 A1 | 10/2010 | Traversaz |
| 2010/0327576 A1 | 12/2010 | Linhorst et al. |
| 2012/0227221 A1* | 9/2012 | Whitaker ........... A61M 39/1011 24/459 |
| 2013/0249212 A1 | 9/2013 | McKiernan |
| 2014/0333068 A1 | 11/2014 | Ikushima |
| 2015/0164206 A1 | 6/2015 | Reed |
| 2015/0211561 A1 | 7/2015 | Whitaker et al. |
| 2016/0053926 A1 | 2/2016 | Whitaker |

FOREIGN PATENT DOCUMENTS

| | | |
|---|---|---|
| CN | 102418810 A | 4/2012 |
| EP | 1397598 B1 | 3/2006 |
| JP | 55-039909 U | 9/1978 |
| JP | 2012-525556 A | 10/2012 |
| JP | 2013-515929 A | 5/2013 |
| WO | 2011/082221 A2 | 7/2011 |

OTHER PUBLICATIONS

CN Office Action dated Sep. 11, 2019 for CN Application No. 201510520934.
European Application No. 15180832.6: Extended European Search Report dated Jan. 7, 2016, 5 pages.

* cited by examiner

REUSABLE CLAMP WITH LATCH RELEASE ARM FOR CONNECTING CONDUIT SECTIONS AND ASSOCIATED METHODS

CROSS REFERENCE TO RELATED APPLICATION

This application is a divisional of U.S. patent application Ser. No. 14/810,960, filed Jul. 28, 2015, and published as U.S. Patent App. Pub. No. 2016/0053926 on Feb. 25, 2016, which claims the benefit of U.S. Provisional Patent App. No. 62/040,150, filed Aug. 21, 2014, the entire disclosures of which are hereby incorporated by reference herein.

TECHNICAL FIELD

This disclosure relates to clamps used when connecting together conduit sections and fittings, such as sanitary fittings that transfer fluids for a manufacturing process, and methods for using such clamps to connect conduit sections.

BACKGROUND

Maintaining sterility in manufacturing processes is often a concern. In one particular example applied in conventional manufacturing settings, receptacles with outlets provided by sanitary fittings are often required to interconnect with other sanitary fittings. These sanitary fittings are typically connected to lengths of conduit sections such as fluid transport tubing, for purposes of transferring contents (typically fluid) from one receptacle to another. To ensure the fluid transfer occurs under sterile conditions, the sanitary fittings at the terminal ends of the fluid transport tubing are clamped together along with a seal or gasket so that the fluid can be transferred between sections of tubing without exposure to the external environment.

Several types of clamps and clamping mechanisms for use with conduit sections and fittings are known. For example, clamps may be molded of a rigid plastic material and formed as a unitary piece or as two separate pieces connected together by coupling mechanisms. These conventional clamps may be awkward to handle as a result of the exterior design of the clamps. As a result, these clamps are capable of over-compression on the conduit sections which may cause a gasket clamped between the conduit sections to extrude out of the fittings (e.g., a catastrophic failure to sterility). In addition, these clamps are typically designed as single use clamps which cannot be disconnected from the fittings without destroying or otherwise damaging the clamping mechanism. In some settings it may be desirable to reuse a clamp with multiple sanitary fittings and conduit sections, but the known clamps do not allow for such reuse.

Conventional clamps and clamping mechanisms also suffer from additional disadvantages. Several types of conventional clamps such as threaded nut adjusted clamps can be difficult to properly secure to the flanges of the fittings in such a manner that the gasket properly seals the two fittings or conduit sections together. Other conventional designs try to avoid the problem of over-compressing the gasket by spacing apart the free ends of a snap-like clamp. However, these designs tend to fail to provide 360 degree coverage around the periphery of the flanges and the gasket, which can also lead to extrusion of the gasket and catastrophic failure of the seal between the conduit sections.

It would be desirable to provide a reusable clamp and method for connecting conduit sections and sanitary fittings that addresses these and other disadvantages of the conventional clamps of the prior art.

SUMMARY

According to one embodiment, a reusable clamp for retaining conduit sections having circular flanges together includes first and second gland members, each including opposing first and second ends and an arcuate internal channel extending between the first and second ends and configured to receive the circular flanges. The first ends are operatively coupled to enable rotation of the gland members relative to one another between an open position and closed position. First and second handles project outwardly from the first and second gland members, and these handles define gripping services for moving between the open and closed positions. A latch finger includes a proximal end that is operatively coupled to the first gland member and a distal end extending beyond the second end of the first gland member. The latch finger includes first locking detents adjacent the distal end and projecting inwardly toward the second gland member. The clamp further includes a retention section including second locking detents that project outwardly from second gland member adjacent to the corresponding second end. The first and second locking detents engage each other in the closed position to prevent movement of the gland members back towards the open position. The clamp also includes a latch release arm that is operably coupled to the latch finger at the distal end and extends to a free end that is located between the first and second handles. The latch release arm is configured to be depressed towards the first handle to force the latch finger to pivot away from the retention section, so that the first locking detents disengage from the second locking detents, thereby enabling the clamp to be reopened and reused, if desired.

In one aspect of the invention, the proximal end of the latch finger is connected to the first handle such that the latch finger is cantilevered over the second end of the first gland member. Moreover, the latch release arm defines a generally arcuate shape between the distal end of the latch finger and the free end. The generally arcuate shape generally follows along the latch finger at one portion and then follows along the first handle at another portion.

In another aspect, the clamp further includes first and second tie-receiving loops that are coupled to the latch release arm and the second handle, respectively. The first and second tie-receiving loops are configured to be tied together in the closed position to prevent the latch release arm from being depressed toward the first handle. The gripping surfaces of the first and second handles may face away from each other in one embodiment, and the latch release arm includes a gripping surface that faces towards the second handle. The first and second tie-receiving loops project from sides of the latch release arm and the second handle that are opposite the gripping surfaces of these elements. Furthermore, the first handle may include an abutment projection extending toward the latch release arm. The abutment projection contacts the second tie-receiving loop to limit further pivoting of the latch finger after the first and second locking detents are disengaged by the latch release arm.

According to another aspect, the first gland member, the handle, the latch finger and the latch release arm are integrally formed as a unitary piece from a resilient plastic material that enables the pivoting movement of the latch finger. Likewise, the second gland member, the second handle and the retention section are also integrally formed as a unitary piece from a resilient plastic material. These two unitary pieces may be formed from the same or different plastic materials. In addition, each of the first and second gland members may include a first stop surface adjacent the hinge assembly and a second stop surface at the corresponding second end. The first stop surfaces and the second stop surfaces are configured to come into abutment with one another in the closed position so as to define a full 360 degree periphery surrounding the circular flanges of the conduit sections being retained together.

In yet another aspect, each of the first and second locking detents includes an angled front surface and a transverse rear surface. The angled front surfaces engage one another to enable the first locking detents to snap over the second locking detents during movement towards the closed position. The transverse rear surfaces engage one another to prevent movement from the closed position until the latch release arm is depressed. In some embodiments the first and second gland members are sized to receive circular flanges associated with 0.75 inch conduit sections. In other embodiments, the first and second gland members are sized to receive circular flanges associated with 1.5 inch conduit sections. Other sizes are also possible within the scope of the invention, depending on the conduit sections employed by the end user. The reusable clamp enables easy closing and opening functionality so that the conduit sections may be sealed together or removed from each other when necessary.

In another embodiment in accordance with the invention, a method for removably connecting two conduit sections having circular flanges together with a clamp includes inserting the circular flanges of the two conduit sections into arcuate internal channels of first and second gland members. The first and second gland members include first and second ends, as well as first and second handles projecting from the gland members, a latch finger coupled to the first gland member and having first locking detents, second locking detents on the second gland member, and a latch release arm coupled to the latch finger. The method also includes closing the clamp by rotating the first and second handles towards one another until the first and second gland members abut at the second ends in the closed position with the first and second locking detents engaged. The method further includes reopening the gland by depressing the latch release arm towards the first handle to disengage the first and second locking detents from one another and then by rotating the first and second handles away from one another until the first and second gland members reach the open position.

In one aspect, the method further includes squeezing gripping surfaces of a latch release arm and the first handle towards one another until the first and second locking detents disengage from one another to thereby enable re-opening of the clamp. In another aspect, depressing the latch release arm to reopen the clamp further includes squeezing the gripping services of the latch release arm and the first handle towards one another until the latch release arm contacts an abutment projection located on the first handle. The method may also include tying first and second tie-receiving loops located on the latch release arm and the second handle together after rotating the first and second handles towards one another to prevent depression of the latch release handle towards the first handle. As a result, the method of these aspects readily allows for opening and re-use of the clamp without destruction of the clamp or the conduit sections retained therein.

These and various additional aspects and features of the present invention will become more readily apparent to those of ordinary skill upon review of the following detailed description taken in conjunction with the drawings of the exemplary embodiments.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION

Figure 1:
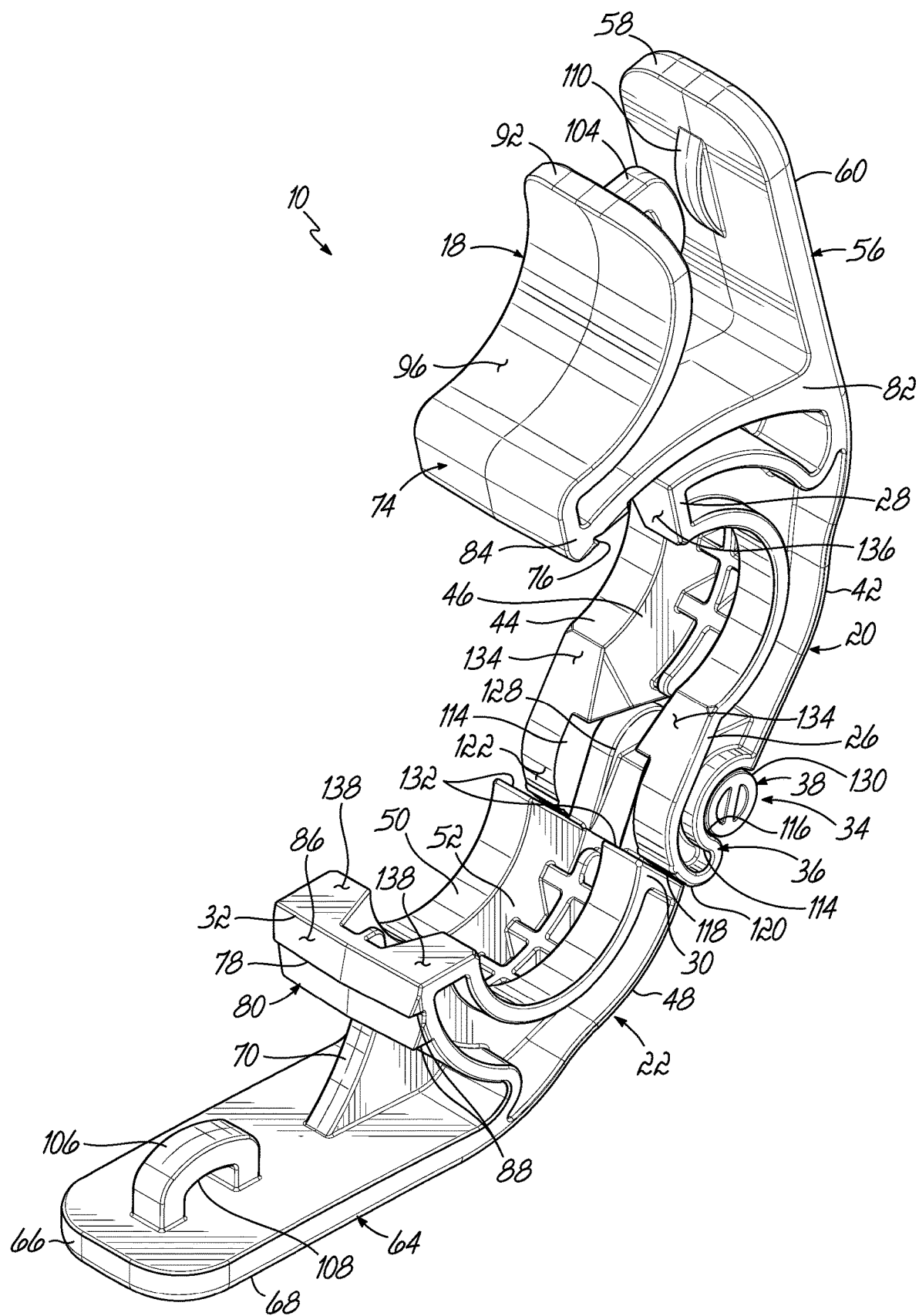
FIG. 1 is a front perspective view of a reusable clamp in accordance with a first embodiment of the invention, the clamp including first and second gland members moved to an open position so as to receive circular flanges of two conduit sections to be connected together.

FIGS. 1 through 6 illustrate a first exemplary embodiment of a clamp 10 used to join together two conduit sections 12 (see FIGS. 5 and 6), which may also be referred to as sanitary fittings in the specific embodiment shown. The clamp 10 is configured to form a circular closure around a circular structure, such as the circular flanges 14 associated with the conduit sections 12 shown in these FIGS., thereby providing equal sealing pressure around the entire circular structure. For example, the clamp 10 may provide equal sealing pressure between two circular flanges 14 and a gasket 16 arranged therebetween. Advantageously, the clamp 10 according to this embodiment is able to be re-opened and reused with different sets of conduit sections 12, should that be desirable for the end user. More particularly, the clamp 10 includes a latch release arm 18 that enables simplified disassembly of the first and second gland members 20, 22 defining the clamp 10 compared to conventional designs. Extra tools and/or specialized equipment are not required to operate the clamp 10 between open and closed positions, and the clamp 10 and conduit sections 12 are not damaged or destroyed by the process of moving the clamp 10 back to the open position. As a result, the clamp 10 may be functional as a single-use clamp 10 or as a reusable clamp 10. Further advantages are evidenced in the detailed discussion of this and other embodiments below.

Figure 2:
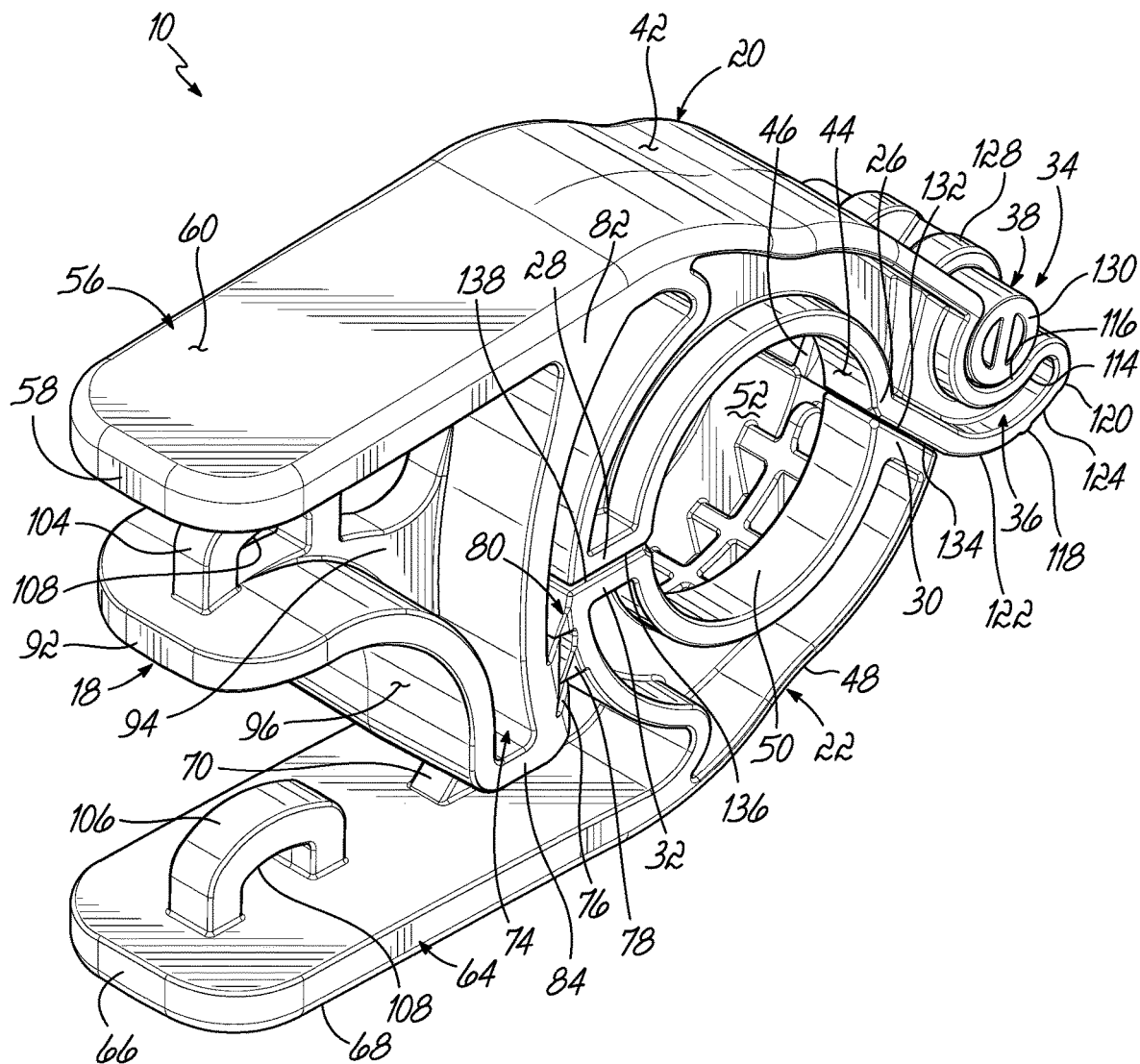
FIG. 2 is a front perspective view of the clamp of FIG. 1, showing the first and second gland members moved to a closed position.

With particular reference to FIGS. 1 and 2, the clamp 10 is shown in an open position and in a closed position, respectively. In this embodiment, the clamp 10 includes the first gland member 20 and the second gland member 22, each of which is generally arcuate between opposing ends. More specifically, the first gland member 20 includes a first end 26 configured to be pivotally coupled to the second gland member 22 and a second end 28 opposite the first end 26. Similarly, the second gland member 22 includes a first end 30 adjacent to the first end 26 of the first gland member 20 and an opposite second end 32. The corresponding first ends 26, 30 of the first and second gland members 20, 22 are detachably joined, for example, by a hinge assembly 34. The hinge assembly 34 includes a barrel-shaped receptacle 36 formed on the first gland member 20 and a hinge pin 38 formed on the second gland member 22. The pivotal engagement of the barrel-shaped receptacle 36 and the hinge pin 38 is described in further detail below, but it will be understood that the clamp 10 may include other structures for pivotally coupling the first ends 26, 30 together in other embodiments consistent with the scope of the invention.

Between the first and second ends 26, 28, the first gland member 20 defines a generally semicircular or arcuate shape including an outer periphery 42 and an inner periphery 44. Located along the inner periphery 44 is a first arcuate inner channel 46 that is sized to receive the circular flanges 14 of the conduit sections 12 upon insertion of those flanges 14 into the clamp 10. In a similar manner, the second gland member 22 defines a generally semicircular or arcuate shape with an outer periphery 48 and an inner periphery 50 extending between the corresponding first and second ends 30, 32. The second gland member 22 also has a second arcuate inner channel 52 located along this inner periphery 50, and the first and second arcuate inner channels 46, 52 combine to form a 360 degree periphery around the circular flanges 14 when the conduit sections 12 are located in the clamp 10 and the clamp 10 is in the closed position. The particular cross-sectional shape of the first and second arcuate inner channels 46, 52 may be modified from the embodiment shown, but in the illustrated embodiment, these arcuate inner channels 46, 52 are configured to wedge the circular flanges 14 towards one another and towards the gasket 16 to form a sealed relationship in the state shown in FIG. 2. In another example, FIG. 1 illustrates that the interior surface of the arcuate inner channels 46, 52 is formed as a grid-like structure so as to save material when molding the first and second gland members 20, 22, but this interior surface could be modified in other embodiments.

As illustrated in FIG. 1, the arcuate inner channels 46, 52 may be exposed in the open position of the clamp 10. In this regard, the clamp 10 may pivot open to a degree that enables the circular flanges 14 of the conduit sections 12 to be placed in the arcuate inner channel 46, 52 of one of the first and second gland members 20, 22. Then the first and second gland members 20, 22 may be moved relative to each other by the hinge assembly 34 to move into the closed position of the clamp 10 so that portions of the arcuate inner channels 46, 52 engage the outer circumference of the circular flanges 14. This arrangement therefore enables the conduit sections 12 to be securely held within the interior of the clamp 10 in the closed position of FIG. 2 (and also shown in FIGS. 5 and 6, described below).

The clamp 10 further includes a first handle 56 projecting outwardly from the outer periphery 42 of the first gland member 20 at a location between the corresponding first and second ends 26, 28. The first handle 56 in this embodiment is a generally elongate and planar member extending from the outer periphery 42 to a free end 58 opposite the junction with the first gland member 20. The first handle 56 extends generally tangentially away from the outer periphery 42 beyond the second end 28 of the first gland member 20, which enables a user to obtain a grip on the first handle 56 when the clamp 10 is to be moved between open and closed positions. For these purposes, the first handle 56 further defines a gripping surface 60 adjacent the free end 58, the gripping surface 60 generally oriented to face away from the remainder of the clamp 10 when the clamp 10 is in the closed position as shown in FIG. 2. A strain relief rib 62 (FIGS. 3A and 3B) may be provided at the junction between the first handle 56 and the outer periphery 42 of the first gland member 20 to increase the strength of this junction and reduce the likelihood of breaking the first handle 56 from the remainder of the clamp 10.

Figure 3A:
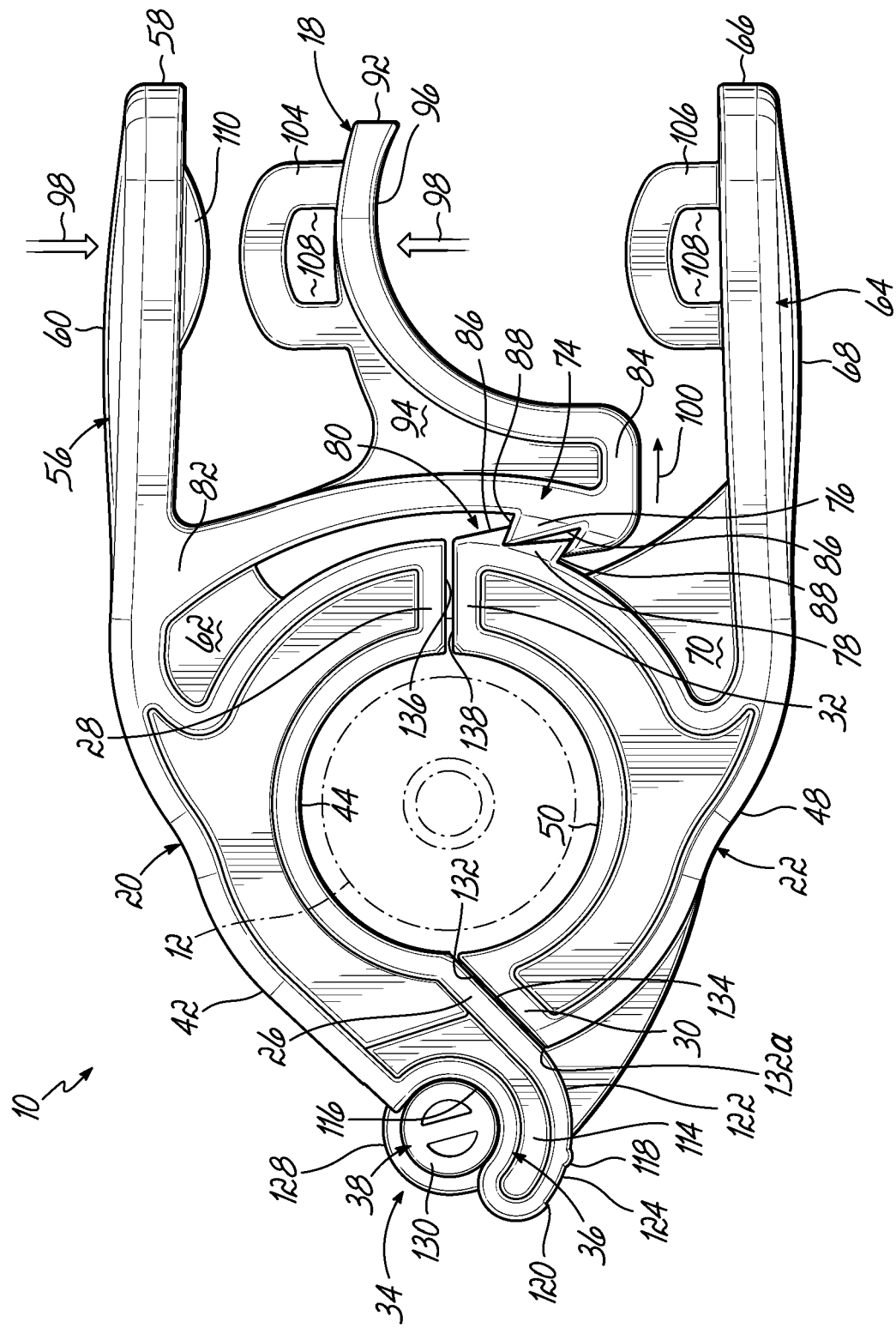
FIG. 3A is a rear side view of the clamp of FIG. 2 in the closed position, with first and second locking detents, respectively located on a latch finger and the second gland member, being engaged with one another.

The clamp 10 also includes a second handle 64 which is largely similar to the first handle 56 but for being located so as to project outwardly from the second gland member 22 instead of the first gland member 20. The second gland member 22 extends from the outer periphery 48 of the second gland member 22 to a free end 66 which extends beyond the second end 32 of the second gland member 22. A gripping surface 68 is located adjacent this free end 66 and faces away from the remainder of the clamp 10 in the closed position, which results in the gripping surfaces 60, 68 on the first and second handles 56, 64 facing away from one another in the closed position as shown in FIG. 3A. As shown in the exemplary embodiment, another strain relief rib 70 may be located at the junction of the outer periphery 48 and the second handle 64.

To close the clamp 10 from the open position shown in FIG. 1, a user grasps the first and second handles 56, 64 at the corresponding gripping surface 60, 68 and squeezes those first and second handles 56, 64 towards one another to pivot the first and second gland members 20, 22 at the hinge assembly 34 until the second ends 28, 32 abut in the closed position as shown in FIG. 2. For example, the first and second handles 56, 64 are configured for a user to grasp with her hand or one or more fingers to enable this pivotal movement of the first and second gland members 20, 22. Once in the closed position, both of the first and second handles 56, 64 extend generally tangentially away from the first and second gland members 20, 22 in the same general direction, such that the first and second handles 56, 64 may be generally parallel to one another in the closed position of the clamp 10. However, it will be appreciated that the specific positioning and angling of the first and second handles 56, 64 may be modified in other embodiments.

In order to reliably retain the clamp 10 in the closed position, the clamp 10 also includes a latch finger 74 extending from the first gland member 20 and having first locking detents 76 that are configured to engage second locking detents 78 provided by a retention section 80 formed on the second gland member 22. In this regard, the latch finger 74 in the illustrated embodiment of the clamp 10 extends from a portion of the first handle 56 located near the junction with the outer periphery 48, to a location beyond the second end 28 of the first gland member 20. Thus, the latch finger 74 is spaced apart from the outer periphery 42 of the first gland member 20 along its length between a proximal end 82 coupled to the first gland member 20 and a distal end 84 opposite the proximal end 82. The latch finger 74 is also positioned to be cantilevered over the second end 32 of the second gland member 22, which allows for snap engagement of the latch finger 74 with the retention section 80. As described in further detail below, the distal end 84 is also connected to the latch release arm 18 which advantageously enables release of the clamp 10 from the closed position when desired by the end user. It will be understood that the latch finger 74 and the proximal end 82 thereof may be connected to other parts of the first gland member 20 in other embodiments. For example, the latch finger 74 may project directly outwardly from the outer periphery 42 and then beyond the second end 28 of the first gland member 20 in one alternative.

Regardless of the particular positioning of the proximal and distal ends 82, 84, the first locking detents 76 are positioned to extend towards the second gland member 22 so as to engage with the second locking detents 78 when the clamp 10 is in the closed position. As shown most clearly in the illustrated embodiment at FIGS. 3A and 3B, the first locking detents 76 extend along a portion of the latch finger 74 adjacent to the distal end 84 thereof. Although two of the first locking detents 76 are shown in this embodiment, more or fewer locking detents may be used in other embodiments, and the first locking detents 76 may be repositioned along the length of the latch finger 74 to match changing configurations of the retention section 80 on the second gland member 22. Each of the first locking detents 76 may protrude radially inwardly as stepped ridges or teeth from the latch finger 74. More specifically, each of the first locking detents 76 includes an angled front surface 86 facing towards the distal end 84 and a transverse rear surface 88 facing towards the proximal end 82, these front and rear surfaces 86, 88 enabling snap-over engagement of the first and second locking detents 76, 78 as set forth in further detail below. It will be understood that the particular angling of the angled front surface 86 and the transverse rear surface 88 may be modified in other embodiments, so long as the configuration of the first locking detents 76 enables an interlocked engagement with the second locking detents 78.

The second locking detents 78 project radially outwardly as stepped ridges or teeth from the outer periphery 48 of the second gland member 22, thereby defining the retention section 80. To this end, the retention section 80 in the exemplary embodiment is located adjacent to the second end 32 of the second gland member 22, which enables the first and second locking detents 76, 78 to immediately begin engaging with each other when the distal end 84 of the latch finger 74 moves over the second end 32 of the second gland member 22 during movement of the clamp 10 from the open position to the closed position. Similar to the first locking detents 76, each of the second locking detents 78 includes an angled front surface 86 facing towards the second end 32 and a transverse rear surface 88 facing away from the second end 32. The angled front surfaces 86 of the first and second locking detents 76, 78 are shaped to ride over each other as the clamp 10 moves to the closed position, at which point the transverse rear surfaces 88 of the first and second locking detents 76, 78 engage each other to prevent movement of the clamp 10 back towards the open position. Once again, the particular shape and angling of the surfaces defining the second locking detents 78 may be modified to match modifications in the first locking detents 76 in other embodiments.

Therefore, when the circular flanges 14 of two conduit sections 12 to be joined together are placed within the first and second arcuate inner channels 46, 52 with the clamp 10 in the open position as shown in FIG. 1, a user can move the clamp 10 to the closed position by grabbing the gripping surfaces 60, 68 of the first and second handles 56, 64 and pushing those first and second handles 56, 64 towards one another. This pushing movement of the first and second handles 56, 64 causes relative rotation of the second ends 28, 32 of the first and second gland members 20, 22 towards one another as a result of the pivotal coupling at the hinge assembly 34. During this pivotal movement, the first locking detents 76 begin snapping over the second locking detents 78 because of the engagement of the angled front surfaces 86 (then causing the transverse rear surfaces 88 to engage with one another). To this end, as the first and second gland members 20, 22 move towards each other from the open position of FIG. 1 to the closed, latched position of FIG. 2, the first and second locking detents 76, 78 may slide along and past each other until the abutting engagement between the second ends 28, 32 is established, which may also correspond to when the most proximal of the first locking detents 76 on the latch finger 74 meshes with a most distal of the second locking detents 78 on the retention section 80. Due to the second ends 28, 32 of the first and second gland members 20, 22 contacting each other in the closed position, only slight clearance at most may be provided between the first and second gland members 20, 22, thereby ensuring a 360 degree periphery surrounding the circular flanges 14. After the first and second handles 56, 64 are squeezed together to make the second ends 28, 32 of the first and second gland members 20, 22 abut in the closed position, the first and second locking detents 76, 78 are fully meshed with one another so that the corresponding transverse rear surfaces 88 engage to retain the clamp 10 in the closed position. This state of the clamp 10 is shown in FIG. 3A, for example.

In some environments, users may desire to re-open the clamp 10 for adjustment or replacement of one or both of the conduit sections 12 being joined. In such a reuse context, it is desirable to provide structure on the clamp 10 to enable easy reopening of the clamp 10, and as described briefly above, this embodiment of the clamp 10 includes such structure at the latch release arm 18. The latch release arm 18 is a generally arcuate member that is coupled to the distal end 84 of the latch finger 74 on an opposite (outward) side of the latch finger 74 from the location of the first locking detents 76. The latch release arm 18 extends for one portion along the latch finger 74 and then bends to extend outwardly for another portion along the first handle 56. To this end, the latch release arm 18 includes a free end 92 that is located between the first and second handles 56, 64 when the clamp 10 is in the closed position. As a result, the latch finger 74 and latch release arm 18 collectively define a generally V-shaped or U-shaped structure connected at the proximal end 82 of the latch finger 74 to the first handle 56 and extending in sequence away from and then back towards the first handle 56. As with the connections of the first and second handles 56, 64 to the first and second gland members 20, 22, a strain relief or strengthening rib 94 may be provided between the latch finger 74 and the latch release arm 18 to ensure that these elements flex as a single piece when reopening the clamp 10. The latch release arm 18 is configured to be used to pull the latch finger 74 out of engagement with the retention section 80 when it is desired to reopen the clamp 10.

The latch release arm 18 defines a gripping surface 96 along the generally arcuate shape between the latch finger 74 and the free end 92. The gripping surface 96 faces towards the second handle 64 in the closed position of the clamp 10 as shown in FIG. 3A. Accordingly, the gripping surface 96 of the latch release arm 18 is located so as to be grasped by a user along with the gripping surface 60 of the first handle 56 when it is desired to disengage the first and second locking detents 76, 78. More specifically, the gripping surfaces 60, 96 of the first handle 56 and the latch release arm 18 are squeezed towards one another by a user as indicated by arrows 98 in FIG. 3A, which causes the latch finger 74 to flex upwardly with the movement of the latch release arm 18 away from the second gland member 22 as shown by arrow 100 in FIG. 3A. Thus, a simple movement or depression of the latch release arm 18 moves the latch release arm 18 towards the first handle 56 and moves the latch finger 74 away from the retention section 80 to the position shown in FIG. 3B. In this position, the transverse rear surfaces 88 of the first and second locking detents 76, 78 have been disengaged from one another by pulling the latch finger 74 radially outwardly away from the retention section 80 on the second gland member 22. In this position, the first and second locking detents 76, 78 no longer prevent pivotal movement of the first and second gland members 20, 22 back towards the open position. As indicated by arrow 102 in FIG. 3B, the user may then pull the squeezed together first handle 56 and latch release arm 18 away from the second handle 64 to thereby rotate the clamp 10 back to the open position. Alternatively, the user may release the latch release arm 18 in the position shown in FIG. 3B to keep the clamp 10 in the closed position, as the latch release arm 18 will automatically flex back to its nominal position with the first and second locking detents 76, 78 engaged with each other. Consequently, the latch release arm 18 enables easy and rapid re-opening of the clamp 10 when that functionality is desired, although the clamp 10 remains reliably secured in the closed position until the latch release arm 18 is depressed. By positioning the free end 92 of the latch release arm 18 between the first and second handles 56, 64, the latch release arm 18 is generally protected from accidental depression until the re-opening is intentionally actuated by a user.

The latch release arm 18 and clamp 10 may include additional elements to help ensure that the latch release arm 18 is not accidentally depressed before the clamp 10 is supposed to be re-opened. To this end, the latch release arm 18 includes a first tie-receiving loop 104 in the form of a U-shaped element extending from an opposite side of the latch release arm 18 as the gripping surface 96. As shown in the illustrated embodiment, the first tie-receiving loop 104 may be located proximate to the free end 92 to extend towards the first handle 56. A second tie-receiving loop 106 is provided on the second handle 64, specifically on the opposite side of the gripping surface 68 thereof. The second tie-receiving loop 106 also defines a U-shaped structure that is located near the free end 66 of the second handle 64 such that the second tie-receiving loop 106 projects towards the latch release arm 18. The first and second tie-receiving loops 104, 106 define apertures 108 that are sized to receive a tying device such as a zip tie (not shown). When a zip tie is wrapped through the first and second tie-receiving loops 104, 106 and tightened, the latch release arm 18 is pulled towards the second handle 64 and away from the first handle 56. As described above, the latch release arm 18 must be depressed towards the first handle 56 to release the engagement of the first and second locking detents 76, 78, so the tying together of the first and second tie-receiving loops 104, 106 therefore prevents release of the latched engagement of the first and second gland members 20, 22 in the closed position. As a result, the tie-receiving loops 104, 106 may be employed to further enhance the retention of the clamp 10 in the closed position until it is desired to re-open the clamp 10, at which point the zip tie can be cut off and then the latch release arm 18 depressed as detailed above. The specific location and shape of the first and second tie-receiving loops 104, 106 may be modified in other embodiments without departing from the functionality or scope of the clamp 10.

Figure 3B:
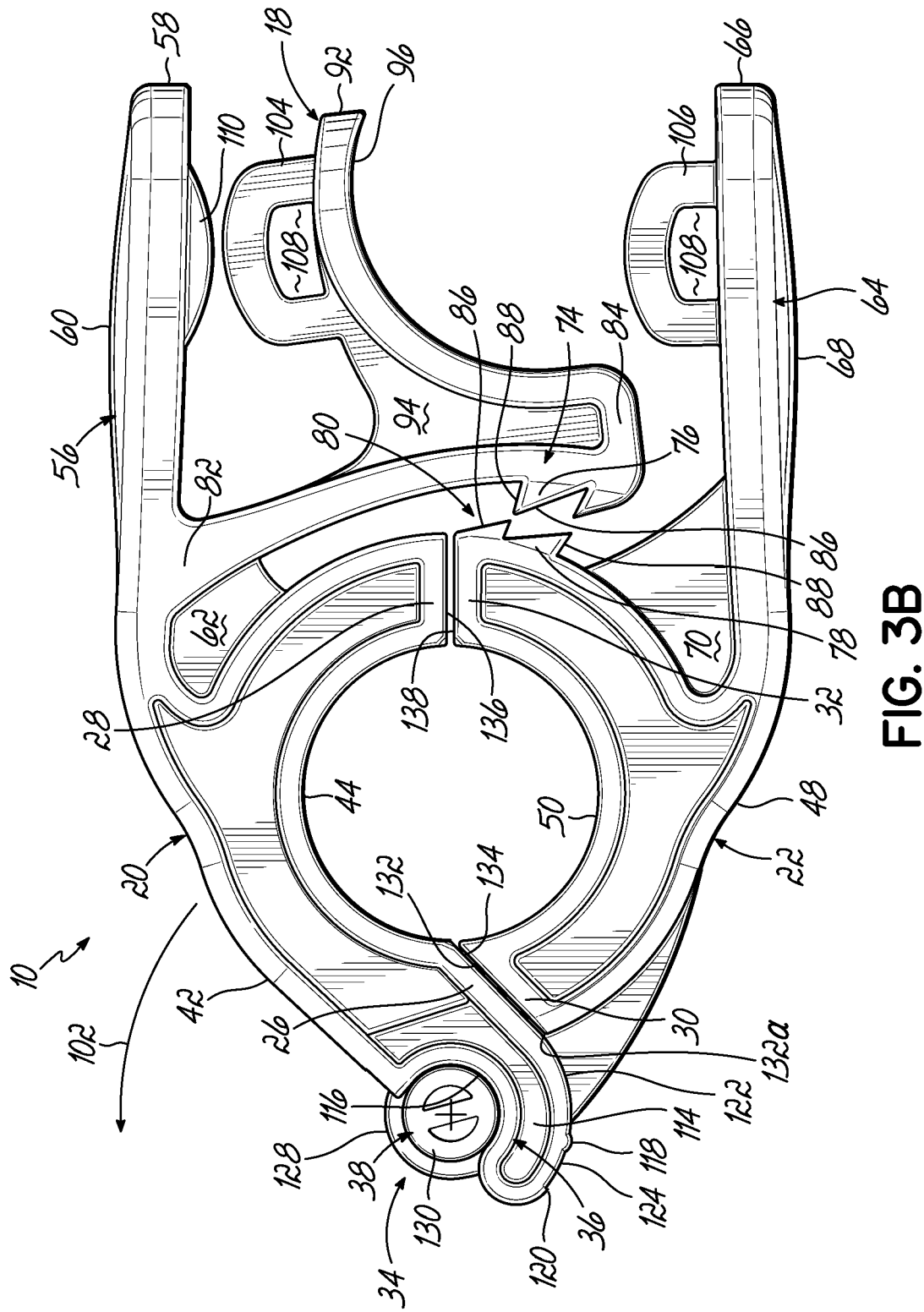
FIG. 3B is a rear side view of the clamp of FIG. 3A with a latch release arm connected to the latch finger being depressed so as to disengage the first and second locking detents from one another.

In some embodiments such as the one illustrated, the first handle 56 of the clamp 10 may further include an abutment projection 110 that extends outwardly from an opposite side of the first handle 56 as the gripping surface 60 thereof. As shown in FIGS. 3A and 3B, the abutment projection 110 therefore extends towards the first tie-receiving loop 104 on the latch release arm 18. The abutment projection 110 is sized to come into abutting engagement with the first tie-receiving loop 104 after the latch release arm 18 has been sufficiently depressed to disengage the first and second locking detents 76, 78 from one another. In this regard, the abutment projection 110 limits depression or flexing movement of the latch release arm 18 and therefore also of the latch finger 74, and this limit on flexing movement ensures that the user does not move the flexible portions of the clamp 10 beyond a breaking limit. Depending on the shape and positioning of the first handle 56 and the latch release arm 18, the abutment projection 110 may be resized, repositioned, or omitted altogether when limiting the movement of the latch release arm 18 is unnecessary.

As alluded to above, the first and second gland members 20, 22 are each integrally molded to be a unitary piece of plastic material such as nylon. These two unitary pieces are shown separated from one another in FIG. 4, for example. In other words, the first gland member 20, the first handle 56, the latch finger 74, and the latch release arm 18 are one unitary piece of material with enough flexibility to enable the flexing or pivoting movement of the latch release arm 18 and latch finger 74 from the remainder of the first gland member 20. The second gland member 22, the second handle 64, and the retention section 80 are also formed as one unitary piece of material with some flexibility. However, both of these unitary pieces are also formed with sufficient rigidity to hold the circular flanges 14 of the conduit sections 12 in reliable sealed engagement when the clamp 10 is in the closed position. The specific materials and method of manufacturing for the first and second gland members 20, 22 may be modified to suit the needs and preferences of end users.

Figure 4:
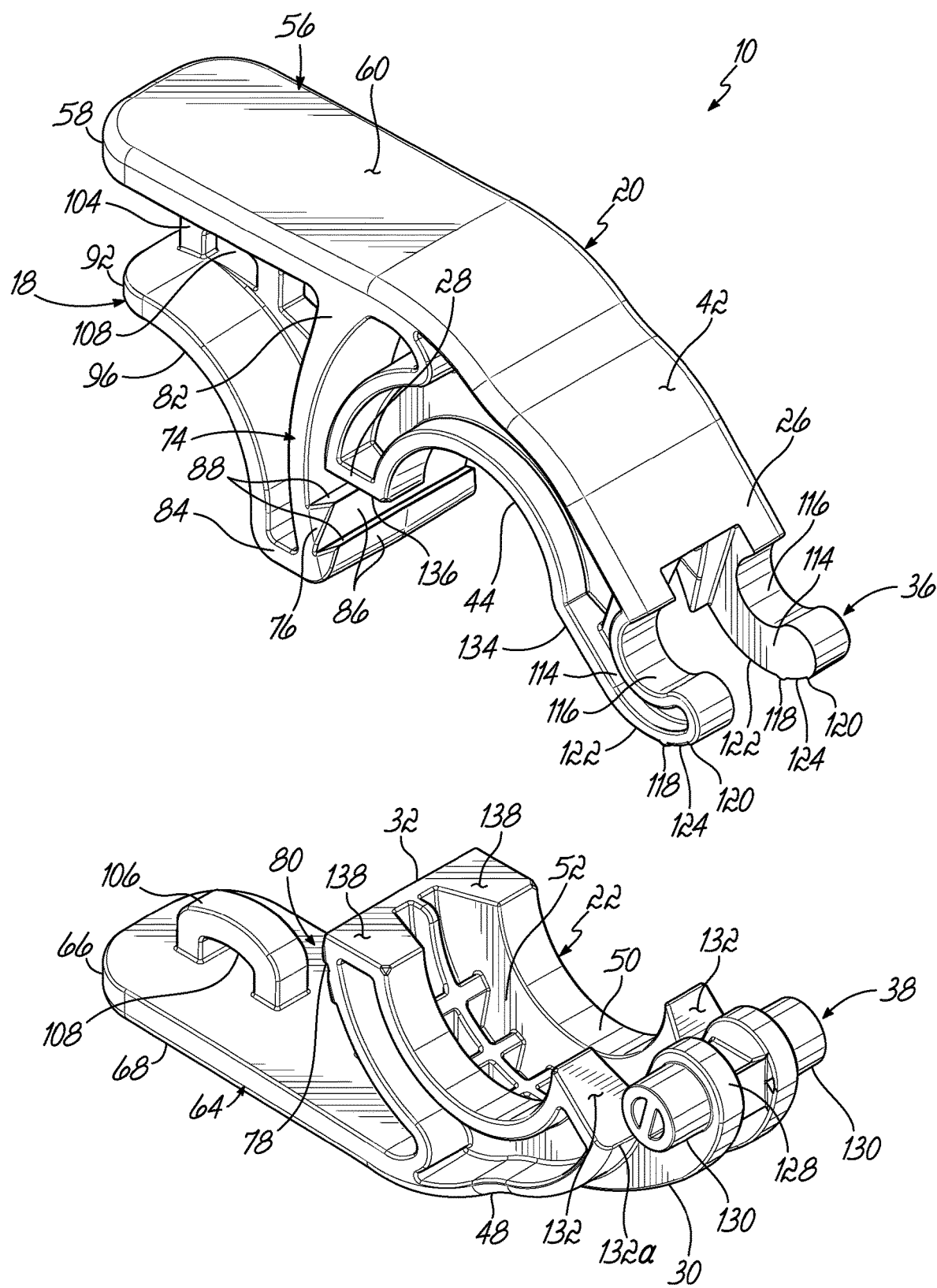
FIG. 4 is a rear side exploded perspective view of the first and second gland members of FIG. 1.

With reference to FIGS. 1 and 4, the hinge assembly 34 located adjacent the corresponding first ends 26, 30 of the first and second gland members 20, 22 will now be described in greater detail. The hinge assembly 34 of the exemplary embodiment shown includes the barrel-shaped receptacle 36 formed on the first gland member 20 and the hinge pin 38 formed on the second gland member 22. As shown in FIG. 4 with the first and second gland members 20, 22 separated, the barrel-shaped receptacle 36 defines the first end 26 of the first gland member 20 and the hinge pin 38 defines the first end 30 of the second gland member 22, although it will be understood that these interconnecting elements may be repositioned relative to the first ends 26, 30 if necessary to provide a different hinged relationship for the clamp 10. Likewise, it will be appreciated that the barrel-shaped receptacle 36 may be formed on the second gland member 22 and the hinge pin 38 formed on the first gland member 20 in other embodiments.

The barrel-shaped receptacle 36 of the hinge assembly 34 may be formed as two arcuate fingers 114 that are configured to be received by the hinge pin 38, as further described below. The arcuate fingers 114 may extend from the first gland member 20 in an arcing direction opposite the arcuate shape of the first gland member 20 (thereby defining a generally S-shaped cross section when viewed from the end thereof). Each arcuate finger 114 of the barrel-shaped receptacle 36 defines a pin-receiving recess 116, a biasing ridge 118, and a stop ridge 120. The pin-receiving recess 116 is formed as a partially cylindrical recess with an open side that faces away from the second gland member 22 in the assembled state of the clamp 10. Each arcuate finger 114 includes an outer curved surface 122 on the opposite side from the pin-receiving recess 116. The biasing ridge 118 is formed as a bump or a ridge extending laterally across a width of the outer curved surface 122 of each of the arcuate fingers 114. The stop ridge 120 may also be formed as a bump or ridge extending laterally across a width of the outer curved surface 122 of each of the arcuate fingers 114, with the stop ridge 120 being located closer to the free end of the arcuate finger 114 than the biasing ridge 118. In this regard, the biasing ridge 118 and the stop ridge 120 may be spaced apart from each other along the arcuate fingers 114, thereby defining a holding recess 124 as the space between the biasing ridge 118 and the stop ridge 120. In the open position of the clamp 10 depicted in FIG. 1, the combination of the biasing ridge 118 and the stop ridge 120 is configured to hold the first and second gland members 20, 22 open relative to one another by engaging with a surface of the second gland member 22 as further described below.

With continued reference to FIG. 4, the structure of the hinge pin 38 on the second gland member 22 includes a supporting hinge flange 128 extending from the second gland member 22 in an opposite direction as the extension direction of the second handle 64. The hinge flange 128 provides structural rigidity and support for a pair of posts 130. In an assembled clamp 10, the arcuate fingers 114 of the first gland member 20 may flank the hinge flange 128 and couple with the posts 130 of the second gland member 22. The pair of posts 130 extends laterally from each side of the hinge flange 128, and the posts 130 are arranged so as to be generally parallel to a central axis through a center of the clamp 10. The posts 130 are received within and cradled by the pin-receiving recesses 116 of the arcuate fingers 114 to function together as the hinge pin 38 for the hinge assembly 34. Accordingly, each post 130 defines an outer diameter that may be approximately the same as an inner diameter of the pin-receiving recesses 116.

At the first end 30 of the second gland member 22, a pair of generally planar first stop surfaces 132 is positioned on opposite lateral sides of a terminal end of the second arcuate inner channel 52. To this end, the first stop surfaces 132 flank the second arcuate inner channel 52 adjacent the first end 30. The pair of posts 130 of the hinge pin 38 are spaced at a distance from the first stop surfaces 132 so as to define a clearance corresponding to a thickness of the arcuate fingers 114 of the barrel-shaped receptacle 36, which enables the arcuate fingers 114 to be inserted in this clearance when coupling the first and second gland members 20, 22 together at the hinge assembly 34. The hinge flange 128 provides a support surface and a guide for the arcuate fingers 114, for example, as the first and second gland members 20, 22 rotate relative to one another.

Similarly, a pair of generally planar first stop surfaces 134 is also provided on opposite lateral sides of a terminal end of the first arcuate inner channel 46 at the first end 26 of the first gland member 20. The first stop surfaces 134 on the first gland member 20 are adjacent to and extend from the junction of the outer curved surfaces 122 of the arcuate fingers 114 from the remainder of the first gland member 20. The first stop surfaces 132, 134 on the first and second gland members 20, 22 are configured to abut one another to close the periphery surrounding the circular flanges 14 of the conduit sections 12 along the first ends 26, 30 of the gland members 20, 22 in the closed position.

On an opposite side of the first and second gland members 20, 22, generally planar second stop surfaces 136, 138 are provided for a similar purpose. More particularly, the first gland member 20 includes a pair of second stop surfaces 136 flanking the sides of another terminal end of the first arcuate inner channel 46. In this regard, the second stop surfaces 136 on the first gland member 20 are located at (and partially define) the second end 28 thereof. Similarly, the second gland member 22 includes a pair of second stop surfaces 138 flanking the sides of another terminal end of the second arcuate inner channel 52, thereby being located at and partially defining the second end 32 of the second gland member 22. The second stop surfaces 136, 138 are configured to abut one another to close the periphery surrounding the circular flanges 14 of the conduit sections 12 along the second ends 28, 32 when the clamp 10 is in the closed position.

In the closed position of the clamp 10, abutting contact between opposing stop surfaces 132, 134 and 136, 138 of the first and second gland members 20, 22 leaves only a slight gap, if any, between the two portions of the clamp 10. As shown in FIGS. 3A and 3B, for example, the first stop surfaces 132, 134 and the second stop surfaces 136, 138 of the first and second gland members 20, 22 are each formed at complementary angles, thereby providing abutting contact in the closed position. These angles relative to the central axis of the clamp 10 may be different in some embodiments for the first stop surfaces 132, 134 as compared to the second stop surfaces 136, 138. As a result of the complementary angles of these elements, the full 360 degree periphery is formed by the first and second gland members 20, 22 when the clamp 10 is in the closed position, and this also prevents over tightening of the clamp 10 and/or the use of insufficient clamping force on the circular flanges 14 of the conduit sections 12. To this end, the 360 degree seal exerts equal sealing pressure around the circumference of the conduit sections 12 and gasket 16 arranged within the clamp 10.

With continued reference to FIGS. 1 and 4, the hinge assembly 34 of this embodiment is configured to hold the clamp 10 in the open position by frictional engagement of the biasing ridge 118 on the arcuate fingers 114 with an edge 132a of the first stop surface 132 of the second gland member 22. More particularly, the edge 132a is configured to be captured in the holding recess 124 between the biasing ridge 118 and the stop ridge 120 formed near the end of the arcuate fingers 114 when the clamp 10 is located in the open position (FIG. 1). The outer curved surfaces 122 of the arcuate fingers 114 rotates or slides smoothly against this edge 132a of the first stop surfaces 132 during most of the rotation between the open and closed positions. However, the provision of the biasing ridge 118 forces the user to apply more force to push this thicker portion of the arcuate finger 114 through the fixed size gap defined between the edge 132a of the first stop surface 132 and the posts 130. Accordingly, when the clamp 10 is in the open position with the edge 132a located in the holding recess 124, a user must apply an increased closing force to the first and second handles 56, 64 to push the biasing ridge 118 through the gap and enable further rotation towards the closed position. In view of this, the biasing ridge 118 effectively prevents unintentional rotation of the clamp 10 from the open position until a user actually applies intentional force to rotate the first and second gland members 20, 22 relative to one another. Thus, the clamp 10 can be maintained in the open position defining the widest possible opening (FIG. 1) for inserting the circular flanges 14 and the gasket 16 when desired, such as during shipping of the clamp 10 to the user. In other words, this configuration makes the clamp 10 ready for immediate use upon receipt by the user.

The stop ridge 120 located on the opposite side of the holding recess 124 from the biasing ridge 118 serves a similar function. To this end, the stop ridge 120 is sized so that it will not move past the edge 132a of the first stop surface 132 unless substantial force is applied to move the stop ridge 120 through the gap defined between the edge 132a and the posts 130. This application of substantial force may be performed, for example, if it is desired to separate the first and second gland members 20, 22 from each other as shown in FIG. 4. Thus, just like the first and second locking detents 76, 78 retain the clamp 10 in the closed position, the interaction of the biasing ridge 118 and the stop ridge 120 with the edge 132a of the first stop surface 132 on the second gland member 22 help retain the clamp 10 in the open position when desired, such as during shipping or during initial setup of the conduit sections 12 and circular flanges 14 in the clamp 10.

From the open position of the clamp 10, the forces used to move the clamp 10 in and out of the open position may be based, in part, on the size and shape of the biasing ridge 118 and the stop ridge 120, on the degree of material flexibility molded into the posts 130 and the edge 132a, and on the forces exerted between the posts 130 of the hinge pin 38 and the pin-receiving recess 116 of the barrel-shaped receptacle 36. In one example, it will be understood that the biasing ridge 118 may be smaller than the stop ridge 120 to provide less resistance to moving from the open position towards the closed position compared to moving from the open position to the separated configuration of FIG. 4. Likewise, the relative sizes and positions of the biasing ridge 118 and the stop ridge 120 may be modified in other embodiments without departing from the scope of the clamp 10 design.

To summarize the operation of the clamp 10, when the first gland member 20 is separated from the second gland member 22, the clamp 10 is assembled by inserting the arcuate fingers 114 of the barrel-shaped receptacle 36 formed on the first gland member 20 into the gap defined between the posts 130 of the hinge pin 38 and the edge 132a of the first stop surface 132 formed on the second gland member 22. Once the stop ridge 120 is forced through this gap, the two gland members 20, 22 are initially assembled in the open position as shown in FIG. 1. In this open position, the second ends 28, 32 of the two gland members 20, 22 are spaced a maximum distance apart to provide a large opening to insert the circular flanges 14 of two conduit sections 12 or sanitary fittings to be coupled together at the clamp 10. To this end, the first and second arcuate inner channels 46, 52 are open to the exterior and ready to receive the circular flanges 14.

The two circular flanges 14 are then inserted, typically with a sealing gasket 16 sandwiched therebetween, into the arcuate inner channels 46, 52 of the first and second gland members 20, 22. In the exemplary embodiment shown in FIGS. 5 and 6, each of the conduit sections 12 is identical and includes a hose barb 142 on one end, followed by a generally conical body 144 that increases in size to the circular flange 14. The circular flange 14 is typically referred to as "circular" because it defines a generally circular outer periphery, although the sidewalls of this circular flange 14 may be shaped to help capture the gasket 16 (FIG. 6) and interact with the arcuate inner channels 46, 52 as shown in the illustrated embodiment. The particular shape of the conduit sections 12 and circular flanges 14 may be modified in other embodiments or uses of the clamp 10, as long as the circular flanges 14 remain sufficiently sized for being captured securely within the first and second gland members 20, 22 when in the closed position.

The clamp 10 is then closed by a user grasping the first and second handles 56, 64 at the corresponding gripping surfaces 60, 68 and moving these handles 56, 64 towards one another to pivot the gland members 20, 22 towards each other at the second ends 28, 32. The initial force applied by the user must be intentional and sufficient to force the biasing ridge 118 past the edge 132a on the first stop surface 132 to move the clamp 10 out of the open position, but the first and second gland members 20, 22 will then rotate smoothly around one another at the hinge assembly 34 following this initial movement. By continuing to pivot the first and second gland members 20, 22 towards each other, the first and second arcuate inner channels 46, 52 will surround and begin to clamp down on the outer periphery of the circular flanges 14 held therein. Furthermore, once the distal end 84 of the latch finger 74 moves past the second end 32 of the second gland member 22, the first and second locking detents 76, 78 begin to snap over each other to lock the clamp 10 in the closed position. The movement to the closed position ends when the second stop surfaces 136, 138 at the second ends 28, 32 of the gland members 20, 22 abut one another, at which point the clamp 10 is in the configuration shown in FIGS. 5 and 6. The total rotation between the open and closed positions can be modified in certain embodiments, but this rotation is about 90 to 120 degrees in the illustrated embodiment of the clamp 10.

Figure 5:
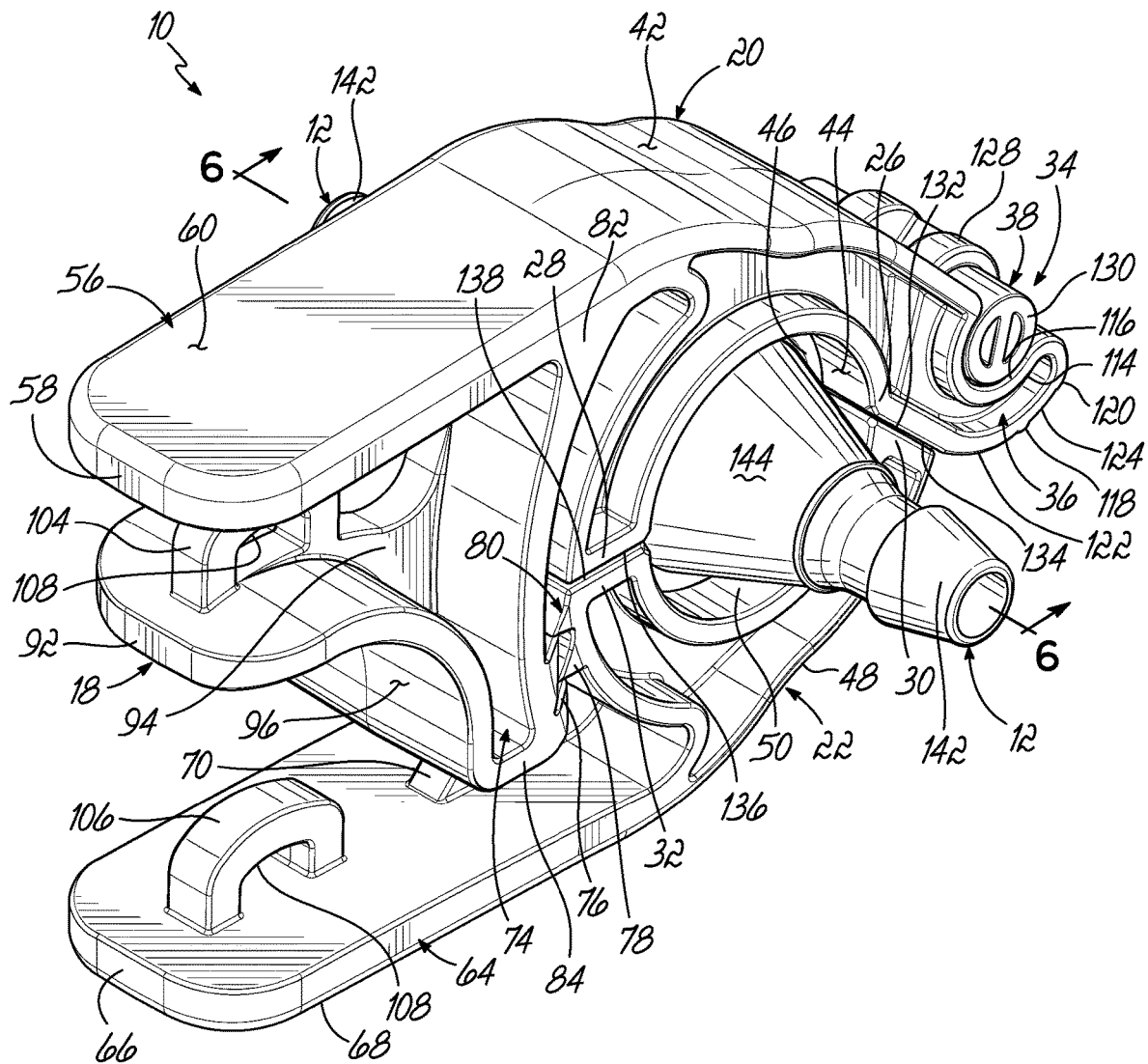
FIG. 5 is a front perspective view of the clamp of FIG. 2 with conduit sections located at least partially in the clamp so as to be held together.
Figure 6:
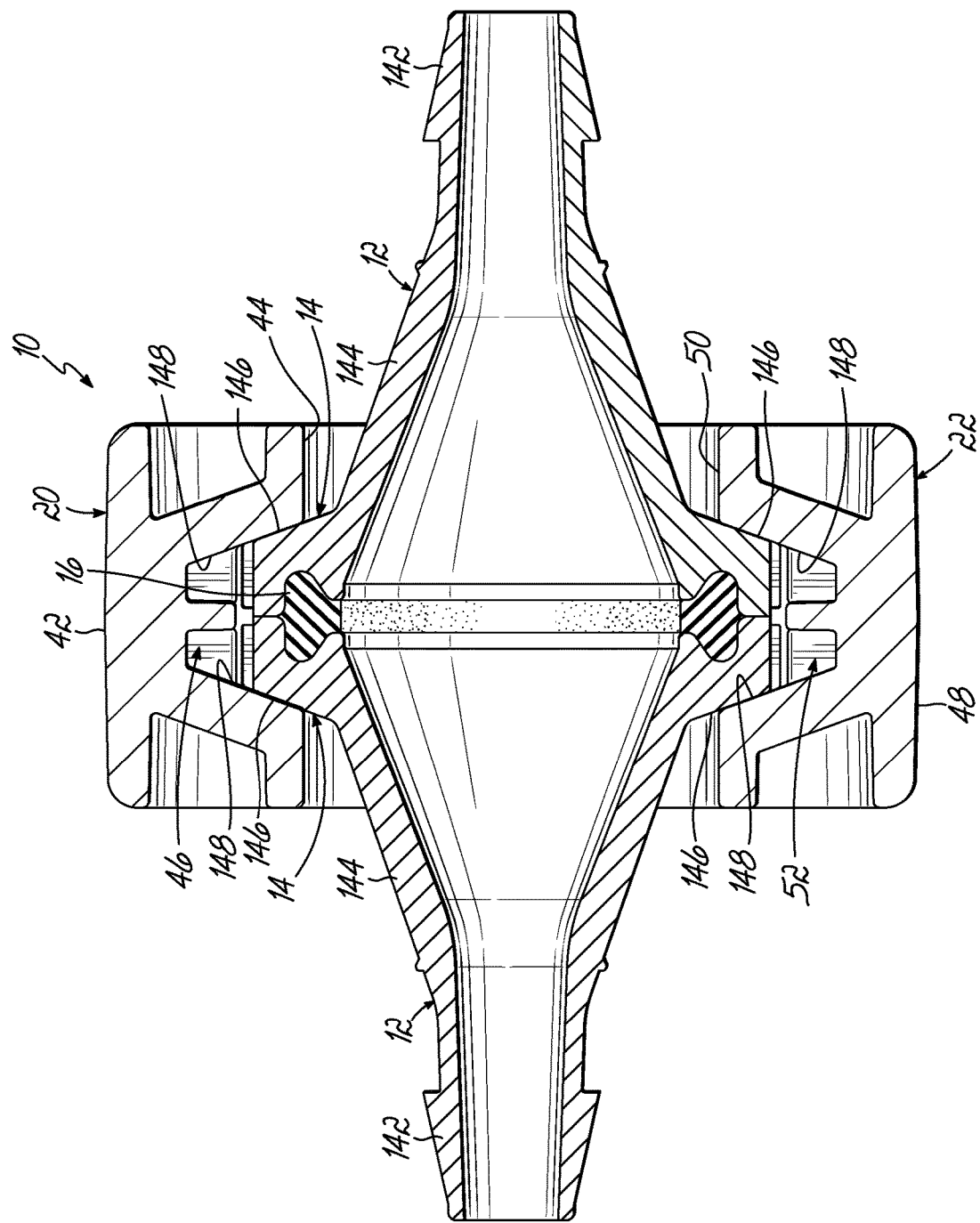
FIG. 6 is a cross-sectional view of the clamp and conduit sections of FIG. 5, taken generally along a central longitudinal axis of the conduit sections so as to show arcuate internal channels of the gland members and the gasket clamped between flanges of the conduit sections.

As shown in FIGS. 5 and 6, the conduit sections 12 are secured together in a sealed relationship when the clamp 10 is moved to the closed position. This sealed relationship is assisted by clamping the gasket 16 between the circular flanges 14, the gasket 16 being formed from a silicone, rubber, or elastomeric material. The circular flanges 14 may include angled exterior surfaces 146 configured to mate with similarly angled side surfaces 148 in the first and second arcuate inner channels 46, 52. In this regard, the circular flanges 14 may frictionally wedge into a tightened or clamped configuration within the arcuate inner channels 46, 52 about an entire 360 degree periphery of the circular flanges 14. The clamp 10 therefore provides roughly equal sealing pressure around the entire 360 degree periphery of the conduit sections 12. Moreover, the limitations on movement at the closed position provided by abutment of the second stop surfaces 136, 138 together helps avoid any over compression of the gasket 16 between the circular flanges 14, which could lead to a catastrophic failure of the sealed arrangement. As a result of wedging or clamping the circular flanges 14 together without over compression, the conduit sections 12 are configured to transmit fluids without leakage as long as the clamp 10 remains in the closed position. In other words, the conduit sections 12 are configured for the sterile transfer of contents from one receptacle to another. The engagement of the first and second locking detents 76, 78 and (optionally) the tying together of the first and second tie-receiving loops 104, 106 with a zip tie ensure that the clamp 10 remains in this closed position during use of the conduit sections 12.

If a user desires that the clamp 10 be re-used with another set of conduit sections 12, or if the conduit sections 12 need to be temporarily separated for any reason, the clamp 10 is reopened by depressing the latch release arm 18 towards the first handle 56, such as by squeezing the corresponding gripping surfaces 60, 96 towards one another. This depression of the latch release arm 18 forces the distal end 84 of the latch finger 74 to lift upwardly out of engagement with the retention section 80 (e.g., the first and second locking detents 76, 78 disengage), and then the user rotates the first and second handles 56, 64 away from one another to move the clamp 10 back to the open position. As with the movement away from the open position, the user will need to apply sufficient force to move the biasing ridge 118 through the gap defined between the posts 130 and the edges 132a of the first stop surfaces 132, at which point the clamp 10 is returned to the state shown in FIG. 1 with the circular flanges 14 free to be removed from the first and second arcuate inner channels 46, 52. Thus, the provision of the latch release arm 18 in the clamp 10 enables a reliable and easy-to-use mechanism for reopening the clamp 10 when that is desired by an end user.

Figure 7:
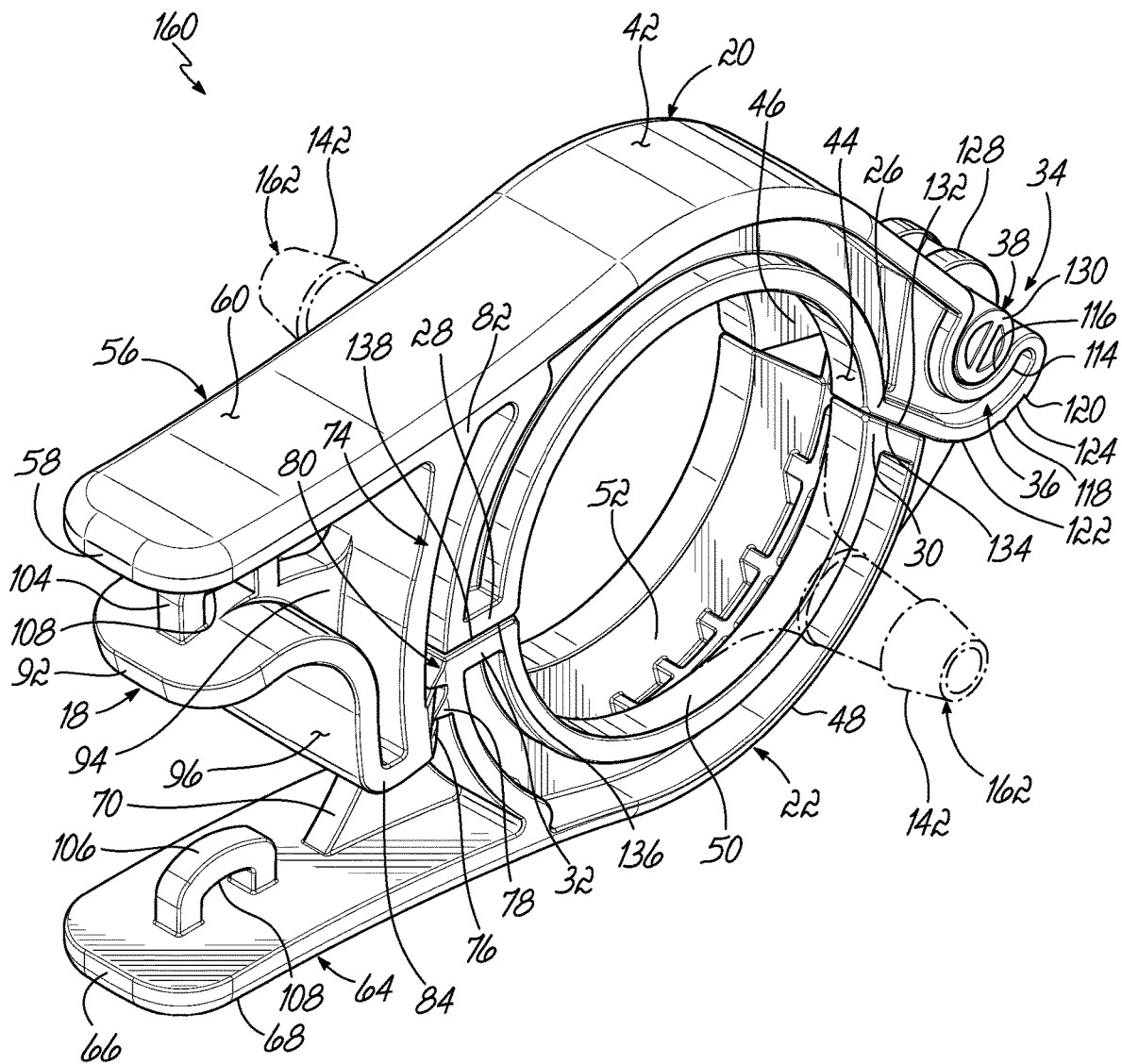
FIG. 7 is a front perspective view of another reusable clamp in accordance with another embodiment, the clamp including first and second gland members in a closed position about two conduit sections (in phantom) to be joined.
Figure 8:
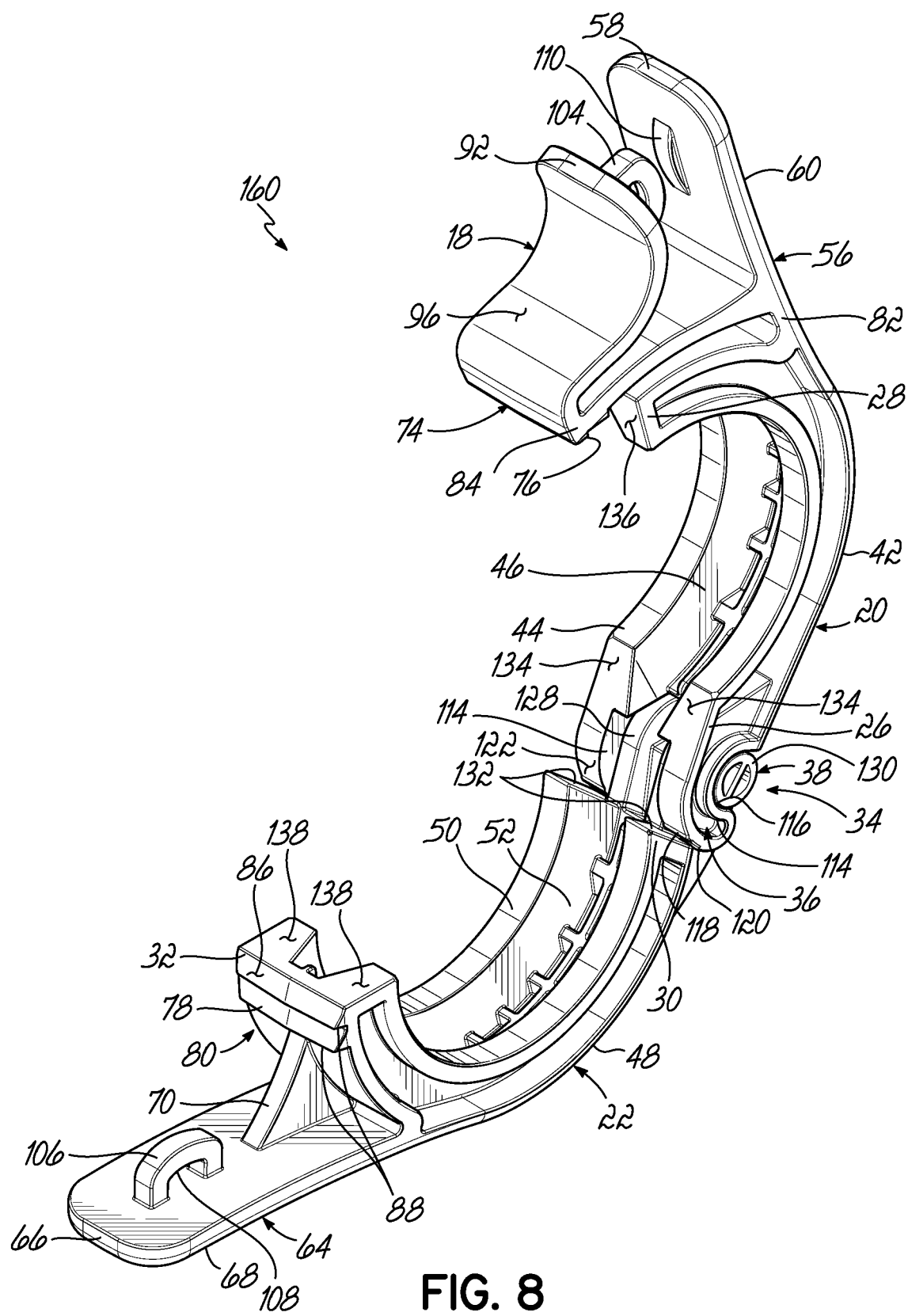
FIG. 8 is a front perspective view of the clamp of FIG. 7, showing the first and second gland members moved to an open position.
Figure 9:
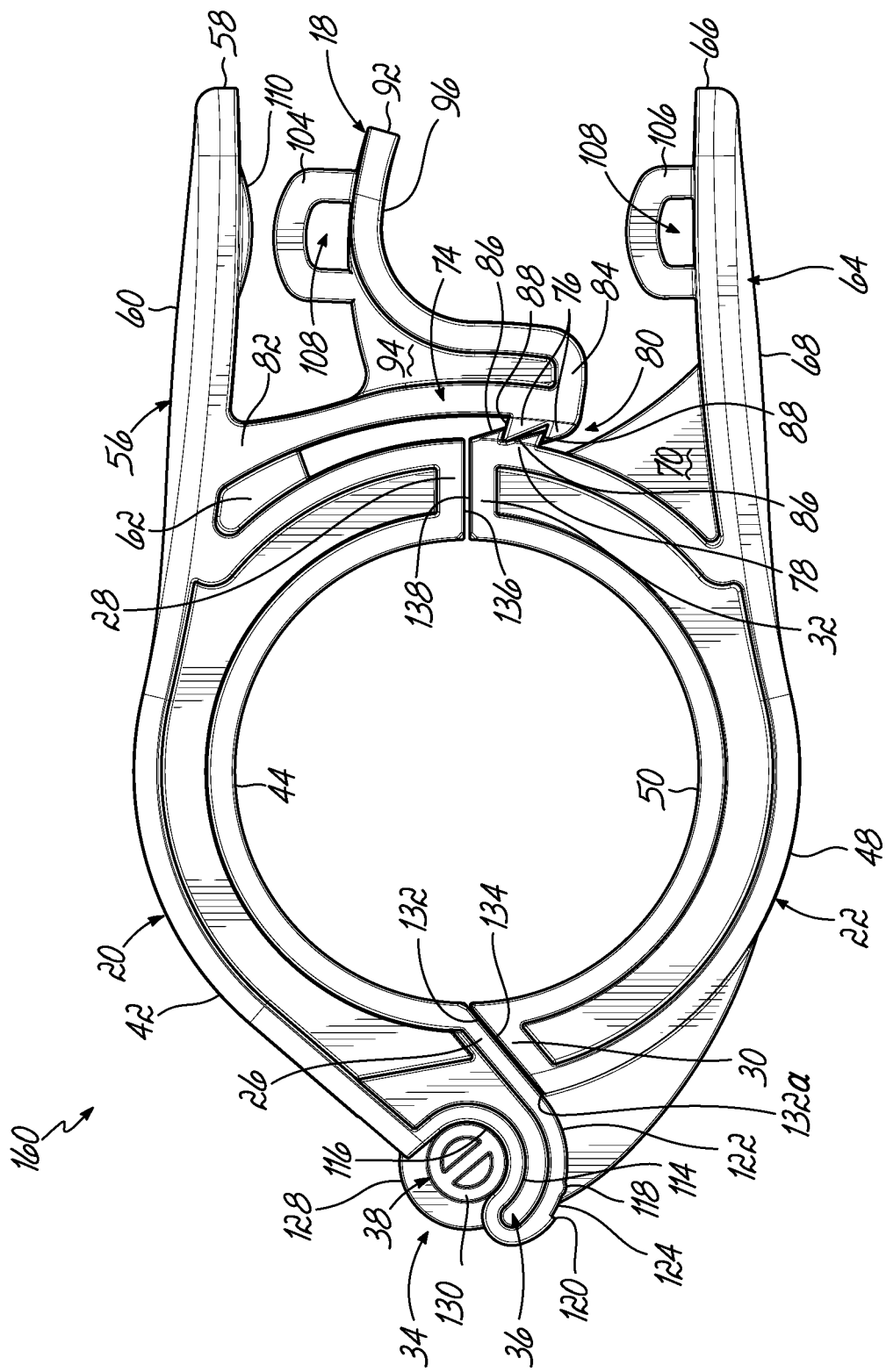
FIG. 9 is a rear side view of the clamp of FIG. 7 in the closed position.

In the embodiment shown in FIGS. 1 through 6 and described above, the conduit sections 12 are 0.75 inch conduit sections 12 that are used in many fields for sanitary transfer of contents. It will be appreciated that the clamp 10 may be resized and reconfigured for other sizes of conduit sections 12 that may be desired for use. For example, another exemplary embodiment of a clamp 160 for use with sanitary fittings and conduit sections 162 is shown in FIGS. 7 through 9. The clamp 160 of this embodiment includes substantially all of the same elements as the previous embodiment, and these elements have been numbered with the same reference numbers for consistency and clarity without further explanation being provided below for these elements. However, it will be appreciated that some of these elements have been resized so that the opening or space encompassed by the first and second arcuate inner channels 46, 52 is larger than that in the first described embodiment. More particularly, the clamp 160 shown in FIGS. 7 through 9 is configured to receive circular flanges 14 associated with 1.5 inch conduit sections 162. Despite these minor changes in appearance and relative locations of elements, the functionality and reusable operation described above for the first clamp 10 are equally applicable in this clamp 160. For example, the clamp 160 may be repeatedly moved between the open position shown in FIG. 8 and the closed position shown in FIGS. 7 and 9 (the larger conduit sections 162 are shown in phantom in FIG. 7). These two embodiments of the clamp 10, 160 are merely two specific examples configured to work with two typical sizes of conduit section used in the sanitary fitting art, but other embodiments are also to be considered within the scope of this disclosure for other known sizes of conduit section.

While the present invention has been illustrated by a description of exemplary embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A reusable clamp for retaining conduit sections having circular flanges together, the reusable clamp comprising:
   first and second gland members, each including opposing first and second ends and an arcuate internal channel extending between said first and second ends and configured to receive the circular flanges, said first ends being operatively coupled together to enable relative rotation of said first and second gland members;
   first and second handles projecting outwardly from said first and second gland members and defining gripping surfaces for moving between an open position and a closed position;
   a latch finger including a proximal end operatively coupled to said first gland member, a distal end extending beyond said second end of said first gland member, and first locking detents adjacent said distal end and projecting inwardly towards said second gland member;
   a retention section including second locking detents projecting outwardly from said second gland member adjacent said corresponding second end, such that said first and second locking detents engage each other in the closed position to prevent movement back to the open position; and
   a latch release arm operatively coupled to said latch finger adjacent said distal end and spaced from the proximal end, the latch release arm being disposed at an outward side of the latch finger opposite the first locking detents, the latch release arm extending to a free end located between said first and second handles, said latch release arm configured to be depressed towards said first handle to force said latch finger to pivot away from said retention section so that said first locking detents disengage from said second locking detents,
   wherein said latch release arm includes a gripping surface facing towards said second handle.

2. The reusable clamp of claim 1, said proximal end of said latch finger being connected to said first handle such that said latch finger is cantilevered over said second end of said first gland member.

3. The reusable clamp of claim 2, said latch release arm defining a generally arcuate shape between said distal end of said latch finger and said free end, the generally arcuate shape generally following along said latch finger at one portion and then along said first handle at another portion.

4. The reusable clamp of claim 1, further comprising:
   first and second tie-receiving loops coupled to said latch release arm and said second handle, respectively, wherein said first and second tie-receiving loops are configured to be tied together in the closed position to prevent said latch release arm from being depressed towards said first handle.

5. The reusable clamp of claim 4, wherein said gripping surfaces of said first and second handles face away from each other, and said first and second tie-receiving loops project from sides of the latch release arm and second handle opposite said gripping surfaces.

6. The reusable clamp of claim 5, said first handle including an abutment projection extending towards said latch release arm, said abutment projection contacting said second tie-receiving loop to limit further pivoting of the latch finger after the first and second locking detents are disengaged.

7. The reusable clamp of claim 1, said first gland member, said first handle, said latch finger, and said latch release arm being integrally formed as a unitary piece from a resilient plastic material that enables pivoting movement of said latch finger, and said second gland member, said second handle, and said retention section being integrally formed as a unitary piece from a resilient plastic material.

8. The reusable clamp of claim 1, further comprising:
a hinge assembly located at said first ends and operatively coupling said first and second gland members together.

9. The reusable clamp of claim 8, each of said first and second gland members including a first stop surface adjacent said hinge assembly and a second stop surface at said corresponding second end, and said first stop surfaces and said second stop surfaces are configured to come into abutment with one another in the closed position so as to define a full 360 degree periphery surrounding the circular flanges.

10. The reusable clamp of claim 1, each of said first and second locking detents including an angled front surface and a transverse rear surface, said angled front surfaces enabling said first locking detents to snap over said second locking detents during movement towards the closed position, and said transverse rear surfaces preventing movement from the closed position until said latch release arm is depressed.

11. The reusable clamp of claim 1, wherein said first and second gland members are sized to receive circular flanges associated with 0.75 inch conduit sections.

12. The reusable clamp of claim 1, wherein said first and second gland members are sized to receive circular flanges associated with 1.5 inch conduit sections.

13. The apparatus of claim 1, wherein at least one of the first gland member and the second gland member includes a reinforcement rib.

14. The apparatus of claim 1, further comprising a gasket between the circular flange structures of each of retaining conduit sections.

* * * * *